United States Patent [19]

Trivedi

[11] Patent Number: 4,994,465
[45] Date of Patent: Feb. 19, 1991

[54] ANTIHYPERLIPIDEMIC AND ANTIATHEROSCLEROTIC TRISUBSTITUTED UREA COMPOUNDS

[75] Inventor: Bharat K. Trivedi, Canton, Mich.

[73] Assignee: Warner-Lambert Company, Morris Plains, N.J.

[21] Appl. No.: 474,426

[22] Filed: Feb. 5, 1990

Related U.S. Application Data

[62] Division of Ser. No. 312,857, Feb. 17, 1989, abandoned.

[51] Int. Cl.$^5$ .................. A61K 31/17; A61K 31/44; C07C 275/28; C07D 213/75
[52] U.S. Cl. .................. 514/256; 514/270; 514/274; 514/333; 514/335; 514/336; 514/337; 514/349; 514/352; 514/357; 514/432; 514/438; 514/456; 514/471; 514/510; 514/564; 514/596; 514/598; 544/316; 544/331; 544/332; 546/261; 546/263; 546/265; 546/274
[58] Field of Search .................. 564/48, 52, 53; 546/296, 297; 544/316, 331, 332; 514/256, 270, 274, 349, 352, 596, 598

[56] References Cited

U.S. PATENT DOCUMENTS

| 3,852,343 | 12/1974 | Krapcho | 564/56 |
| 4,387,106 | 6/1983 | DeVries et al. | 424/322 |
| 4,397,868 | 8/1983 | DeVries et al. | 424/322 |
| 4,623,662 | 11/1986 | DeVries | 514/596 |

FOREIGN PATENT DOCUMENTS 293880 12/1988 European Pat. Off. .
2149394A 6/1986 United Kingdom .

Primary Examiner—Richard L. Raymond
Attorney, Agent, or Firm—Ronald A. Daignault

[57] ABSTRACT

Certain trisubstituted urea compounds as potent inhibitors of the enzyme acyl-CoA:cholesterol acyltransferase, their method of manufacture, pharmaceutical compositions containing such compounds as well as methods of inhibiting the interstitial absorption of cholesterol and lowering blood plasma cholesterol with such compounds as described.

14 Claims, No Drawings

ANTIHYPERLIPIDEMIC AND ANTIATHEROSCLEROTIC TRISUBSTITUTED UREA COMPOUNDS

This is a divisional of U.S. application Ser. No. 313,857, filed Feb. 17, 1989, now abandoned.

BACKGROUND OF THE INVENTION

This invention relates to chemical compounds having pharmacological activity, to pharmaceutical compositions which include these compounds, and to a pharmaceutical method of treatment. More particularly, this invention concerns certain trisubstituted urea compounds which inhibit the enzyme acyl-coenzyme A:-cholesterol acyltransferase (ACAT), pharmaceutical compositions containing these compounds, and a method of inhibiting intestinal absorption of cholesterol or of regulating cholesterol.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesterol esters plus triglycerides and an exterior consisting primarily of phospholipids and a variety of types of protein which are recognized by specific receptors. For example, cholesterol is carried to the sites of deposit in blood vessels in the form of low density lipo-protein cholesterol (LDL cholesterol) and away from such sites of deposit by high density lipo-protein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

U.S. Pat. No. 4,387,106 to DeVries, et al. discloses methods for treating atherosclerosis using certain trisubstituted N-[substituted(phenyl)]-N',N]-diarylalkyl urea and thiourea compounds.

U.S. Pat. No. 4,397,868 to DeVries, et al. discloses methods for treating atherosclerosis using certain trisubstituted urea compounds.

U.S. Pat. No. 4,623,662 to DeVries discloses a method of reducing arterial wall deposits of cholesterol employing certain trisubstituted urea and thiourea compounds.

United Kingdom Patent Application No. 2149394A to DeVries also discloses certain trisubstituted ureas as antiatherosclerotic agents.

The compounds of the present invention are also trisubstituted ureas but with distinct substituents from the DeVries patents and publications.

SUMMARY OF THE INVENTION

The present invention provides a class of compounds with ACAT inhibitory activity having the formula $$\text{formula I}$$

wherein
$R_1$, $R_2$, and $R_3$ can independently be hydrogen, alkyl of one to six carbon atoms, halogen or alkoxy of one to six carbon atoms;
A is either —CH or N;
$R_4$ is alkyl of four to ten carbon atoms, cycloalkyl of three to seven carbon atoms, benzyl substituted by alkyl of one to six carbon atoms, alkoxy of one to six carbon atoms, halogen, COOR' where R' is H or alkyl, $NR_1'R_2'$ where $R_1'$ and $R_2'$ can independently be hydrogen, alkyl or cycloalkyl of three to seven carbon atoms;
$R_5$ is selected from the group of the formulae $$\text{II} \quad \text{III} \quad \text{IV}$$

wherein
n is zero, one or two;
n' is an integer of from two to six;
n" is zero or one;
Ar is phenyl, naphthyl, pyridyl, thienyl or furanyl optionally substituted by alkyl of from one to six carbon atoms, hydroxy, alkoxy of one to six carbon atoms, benzyloxy, chlorine, fluorine, bromine, nitro, trifluoromethyl, $NHCOCH_3$, —$CONH_2$, —COOH, —COO—alkyl, —$CH_2COOH$, —$CH_2CONH_2$ or $NR_1'R_2'$ where $R_1'$ and $R_2'$ is as defined above;
X is —$CH_2$, O, S, SO, or $SO_2$;
$R_6$ and $R_7$ can independently be alkyl of from one to six carbon atoms, hydroxy, alkoxy of from one to six carbon atoms, benzyloxy, halogen, nitro, trifluoromethyl, —COOH, —$CONH_2$, COO alkyl, in which alkyl is from one to six carbon atoms or $NR_1'R_2'$ where $R_1'$ and $R_2'$ are as defined above;

with the proviso that when $R_5$ is of the formula III, Ar cannot be naphthyl, and pharmaceutically acceptable acid addition or base salts thereof.

DETAILED DESCRIPTION

The compounds of the present invention form a class of substituted ureas having potent activity as inhibitors of the enzyme acyl CoA:cholesterol acyltransferase (ACAT).

In the urea compounds of the present invention, the first nitrogen atom is monosubstituted by an aromatic or heteroaromatic ring system selected from phenyl, pyridyl, or pyrimidyl. These are unsubstituted or, alternatively, substituted with one, two, or three groups, $R_1$, $R_2$, and $R_3$ selected independently from alkyl of from one to six carbon atoms, alkoxy of from one to six carbon atoms or halogen, preferably fluorine, chlorine or bromine. Preferred compounds are those in which the aromatic ring system is phenyl or substituted phenyl.

In this invention, the second nitrogen atom is substituted as $R_5$ in formula I which may be an aryl-substituted cycloalkyl ring of formula II which may be attached directly to the nitrogen atom, or may be separated from the nitrogen atom by a bridging group of up to two methylene (i.e., —$CH_2$—) groups. The cycloalkyl ring is cyclopropyl, cyclobutyl, cyclopentyl, cyclohexyl, or cycloheptyl, with cyclopentyl and cyclohexyl being preferred, cyclopentyl being most preferred.

The cycloalkyl ring is further substituted, at the same atom of attachment to the nitrogen of the urea moiety or the same atom of attachment to the methylene bridge, by an aryl group. This aryl group is unsubstituted phenyl, naphthyl, pyridyl, thienyl or furanyl optionally substituted by one, two, or three groups independently selected from alkyl of from one to six carbon atoms, alkoxy of from one to six carbon atoms, benzyloxy, hydroxy, fluorine, chlorine, bromine, nitro, trifluoromethyl, —NH—$COCH_3$, —$CONH_2$, —COOH, —COO—alkyl (where alkyl is from one to six carbon atoms), —$CH_2COOH$, or —$CH_2CONH_2$, or —$NR_1'R_2'$ in which $R_1'$ and $R_2'$ are independently hydrogen or alkyl of from one to six carbon atoms.

An alternate $R_5$ substituent at the second nitrogen atom of the urea moiety of compounds of this invention is a diarylalkyl group of formula III in which the aryl groups may each be unsubstituted phenyl, naphthyl, thienyl, furanyl, or pyridyl groups or phenyl, naphthyl, thienyl, furanyl, or pyridyl groups substituted with alkyl of from one to six carbon atoms, alkoxy of from one to six carbon atoms, hydroxy, fluorine, chlorine, bromine, trifluoromethyl, nitro benzyloxy, —NH-$COCH_3$, —$CONH_2$,—, COOH, —COO—alkyl, —$CO_2$-COOH, —$CH_2CONH_2$ or $NR_1'R_2'$ where $R_1'$ and $R_2'$ are as defined above.

In those cases where Ar are both selected from groups other than phenyl or substituted phenyl as defined above, the preferred values of n is one and zero, respectively.

Excluded are compounds where each Ar is naphthyl.

Still another alternate $R_5$ substituent on the second nitrogen atom of the urea moiety of compounds of this invention and of formula I as substituted by $R_5$ is a bicyclic group of the formula IV which may be either directly attached to the second nitrogen, or may be attached through an alkylene linkage, i.e., —$CH_2$—.

In the group of formula IV, X is —$CH_2$—, O, S, SO or $SO_2$ and $R_6$ and $R_7$ are substituents on the ring and can each independently be alkyl of from one to six carbon atoms, hydroxy, alkoxy of from one to six carbon atoms, benzyloxy, halogen, preferably fluorine, chlorine or bromine, nitro, trifluoromethyl, —COOH, —$CONH_2$, —COO—alkyl in which alkyl is from one to six carbon atoms, or $NR_1'R_2'$ where $R_1'$ and $R_2'$ are each hydrogen or alkyl of from one to six carbon atoms.

Preferred compounds of the present invention and of formula I are those in which $R_4$ is alkyl of from four to ten carbon atoms or benzyl and $R_5$ is a group of formula II, wherein n is one; n' is 4 or 5, and Ar is phenyl, naphthyl, pyridyl, thienyl, or furanyl, especially phenyl.

Also preferred are compounds of formula I in which $R_5$ is a group of formula III in which Ar is phenyl, or a group of formula IV in which $R_6$ and $R_7$ are hydrogen.

Most preferred are the compounds of formula I as defined above where $R_1$, $R_2$, and $R_3$ are each independently hydrogen, alkyl of from one to six carbon atoms, fluorine or chlorine.

Particularly valuable are the following:

N'-(2,4-difluorophenyl)-N-benzyl-N-[(2,2-diphenyl)-ethyl]urea;

N'-[(2,6-dimethyl)phenyl]-N-benzyl-N-[(2,2-diphenyl)-ethyl]urea;

N'-[2,6-bis(1-methylethyl)phenyl]-N-benzyl-N-[(2,2-diphenyl)ethyl]urea;

N'-(2,4-difluorophenyl)-N-benzyl-N-[(1-phenylcyclopentyl)methyl]urea;

N'-(2,6-dichlorophenyl)-N-benzyl-N-[(1-phenylcyclopentyl)methyl]urea;

N'-(2,4,6-trimethylphenyl)-N-benzyl-N-[(1-phenylcyclopentyl)methyl]urea;

N'-[2,6-bis(1-methylethyl)phenyl]-N-benzyl-N-[(1-phenylcyclopentyl)methyl]urea;

N'-[(2,6-dimethyl)phenyl]-N-benzyl-N-[(1-phenylcyclopentyl)methyl]urea;

N'-[(2,6-bis(1-methylethyl)phenyl]-N-heptyl-N-[(1-phenylcyclopentyl)methyl]urea;

N'-[(2,6-dimethyl)phenyl]-N-heptyl-N-[(1-phenylcyclopentyl)methyl]urea;

N'-(2,4-difluorophenyl)-N-heptyl-N-[(1-phenylcyclopentyl)methyl]urea;

N'-[2,6-dimethyl)phenyl)]-N-heptyl-N-[(2,2-diphenyl)ethyl]urea; and

N'-(2,4-difluorophenyl)-N-heptyl-N-[(2,2-diphenyl)ethyl]urea.

By the term "lower alkyl" or "alkyl" as used throughout this specification and the appended claims is meant a branched or unbranched hydrocarbon grouping derived from a saturated hydrocarbon, and unless specified otherwise, of from one to six carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

By the term "alkoxy" is meant a lower alkyl group, as defined above, attached to the parent molecular moiety through an oxygen atom.

Cycloalkyl of three to seven carbon atoms is cyclopropyl, cyclobutyl, cyclopentyl, cyclohexyl or cycloheptyl.

The compounds of this invention may exist in different enantiomorphic forms due to the presence of one or more asymmetric centers in the molecule. This invention contemplates al enantiomorphic forms of the compounds as well as mixtures thereof including racemic mixtures. Individual enantiomers may be obtained, if desired, by resolution techniques known to the art as, for example, formation of diastereomers and fractional recrystallization or resolution on chiral chromatographic columns.

In those instances where the compounds of the present invention bear a basic nitrogen atom as, for example, when Ar is substituted by amino, alkylamino, or dialkylamino, or when Ar is pyridyl, the compounds are capable of forming acid addition salts. These acid addition salts are also contemplated as falling within the scope of this invention.

While the acid addition salts may vary from the free base form of the compounds in certain properties such as melting point and solubility, they are considered equivalent to the free base forms for the purposes of this invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts. (See, for example, Stephen N. Berge, et al, *J. Pharm. Sciences*, 66:1–9 (1977).

In those cases where the compounds of the present invention bear an acidic functional group, as for example, when the polycyclic moiety is substituted by carboxyl, the compounds are capable of forming base addition salts with pharmaceutically acceptable metal cations and bases. Suitable metals are aluminum, calcium, lithium, magnesium, potassium, sodium, and zinc. Suitable bases are ammonia and organic amines which are sufficiently strong bases to form salts with the carboxyl group.

The metal salts and base addition salts may be generated from the acid form of the compounds by reaction of the latter with one equivalent of a suitable nontoxic, pharmaceutically acceptable metal hydroxide, carbonate, or bicarbonate, followed by evaporation of the solvent employed for the reaction and recrystallization of the salt, if required. The free acid may be recovered from the metallic salt or base addition salt by reaction of a water solution of the salt with a suitable acid such as dilute aqueous hydrochloric acid.

The class of metals, acids, and organic amine bases suitable for the formation of nontoxic, pharmaceutically acceptable salts of the compounds of this invention is well known to practitioners of the pharmaceutical formulation arts. (See, for example, Stephen N. Berge, et al, *J. Pharm. Sciences* 66:1–19 (1977)).

While the salts may vary from the free base or free acid forms of the compounds of this invention in certain properties such as melting point and solubility, they are considered equivalent for the purposes of this invention.

In those instances where the compounds of the present invention bear a basic nitrogen atom in a heterocyclic group as, for example, when Ar is pyridyl, the compounds are capable of forming N-oxides. These N-oxides are also contemplated as falling within the scope of this invention.

The N-oxides may be prepared from the free base forms of the compounds by reaction of the latter with an oxidizing agent, such as, for example, hydrogen peroxide, peracetic acid or perbenzoic acid in a suitable solvent.

Further, the compounds of this invention may exist in unsolvated as well as solvated forms with pharmaceutically acceptable solvents such as water ethanol, and the like. In general, the solvated forms are considered equivalent to the unsolvated forms for the purposes of this invention.

The compounds of the present invention are prepared by a general method which comprises reacting the appropriately substituted isocyanate of the formula

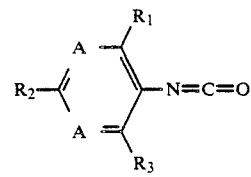

with the appropriate di-substituted amine of the formula

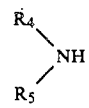

in which A, $R_1$, $R_2$, $R_3$, $R_4$, and $R_5$ are as defined above.

The reaction is generally carried out in a polar aprotic organic solvent such as ethyl acetate, at any temperature between room temperature and the boiling point of the solvent, with room temperature being preferred.

The reaction is allowed to proceed until analysis of the mixture by a means such as chromatography indicates that the reaction is substantially complete. Reaction times may vary between about two hours to about 24 hours, depending upon the particular reagents and reaction temperature employed. The starting isocyanate compounds are known or commercially available or, if not previously known, are prepared by methods well known in the art from the corresponding amine compounds.

The di-substituted amines are prepared by generally known methods which comprise either reacting an amine of the formula $R_4NH_2$ with a $R_5$-halide in the presence of base, i.e., triethylamine, or, alteratively, reacting a corresponding $R_4$-halide with an amine of the formula $R_5NH_2$.

The reaction takes place in the presence of base, where the base, if organic, can also be a solvent, or in an inert organic solvent, e.g., tetrahydrofuran, and at room to elevated temperatures, preferably at the boiling point of the solvent.

The starting amines and halides are either known or prepared by known methods. Many of the $R_5$ $NH_2$ compounds have been described in European Publication No. 293880 or in our copending applications Ser. Nos. 176,079, 175,089, and 176,080, all filed on Mar. 30, 1988, and incorporated herein by reference.

As shown by the data presented below in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the inhibition of intestinal absorption of dietary cholesterol, the reabsorption of cholesterol released into the intestine by normal body action, or the modulation of cholesterol.

IN VITRO TESTS

The ability of representative compounds of the present invention to inhibit ACAT was measured using an in vitro test more fully described in Field, F. J. and Salone, R. G., *Biochemica et Biophysica* 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed in $IC_{50}$ values; i.e., the concentration of test compound required to inhibit 50% expression of the enzyme.

TABLE 1

| Example No. | $R_1$ | $R_2$ | $R_3$ | $R_4$ | $R_5$ | [$IC_{50}$ μM] |
|---|---|---|---|---|---|---|
| 1 | F | F | H | benzyl | $-CH_2-CH(Ph)(Ph)$ | 0.29 |
| 2 | $CH_3$ | H | $CH_3$ | benzyl | $-CH_2-CH(Ph)(Ph)$ | 1.37 |
| 3 | i-Pr | H | i-Pr | benzyl | $-CH_2-CH(Ph)(Ph)$ | 1.3 |
| 4 | F | F | H | benzyl | $-CH_2-$cyclopentyl(Ph) | 0.090 |
| 5 | Cl | H | Cl | benzyl | $-CH_2-$cyclopentyl(Ph) | 0.051 |
| 6 | $CH_3$ | $CH_3$ | $CH_3$ | benzyl | $-CH_2-$cyclopentyl(Ph) | 0.080 |
| 7 | i-Pr | H | i-Pr | benzyl | $-CH_2-$cyclopentyl(Ph) | 0.17 |
| 8 | $CH_3$ | H | $CH_3$ | benzyl | $-CH_2-$cyclopentyl(Ph) | 0.059 |
| 9 | i-Pr | H | i-Pr | heptyl | $-CH_2-$cyclopentyl(Ph) | 0.11 |
| 10 | $CH_3$ | H | $CH_3$ | heptyl | $-CH_2-$cyclopentyl(Ph) | 0.061 |
| 11 | F | F | H | heptyl | $-CH_2-$cyclopentyl(Ph) | 0.31 |
| 12 | $CH_3$ | H | $CH_3$ | heptyl | $-CH_2-CH(Ph)(Ph)$ | 1.3 |
| 13 | F | F | H | heptyl | $-CH_2-CH(Ph)(Ph)$ | 0.17 |

Structure for Table 1:

$$R_2\text{-Ar}(R_1)(R_3)\text{-NH-C(=O)-N}(R_4)(R_5)$$

In therapeutic use as agents for the inhibition of intestinal absorption of cholesterol, or as hypolipidemic or hypocholesterolemic agents, the compounds utilized in the pharmaceutical method of this invention are administered to the patient at dosage levels of from 250 to 1000 mg per day. For a normal human adult of approximately 70 kg of body weight, this translates into a dosage of from 5 to 20 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following preparative examples are provided to enable one skilled in the art to practice the invention, and are illustrative thereof. They are not to be read as limiting the scope of the invention as it is defined by the appended claims.

EXAMPLE 1

Preparation of
N'-(2,4-difluorophenyl)-N-benzyl-N-[(2,2-diphenyl)ethyl]urea.

Step A: Preparation of N-benzyl-2,2-diphenyl ethyl-amine.

To a solution of 2,2-diphenyl ethyl amine (10.0 g, 0.051 mol) and triethyl amine (20.5 g, 0.203 mol) in 200 mL tetrahydrofuran was added a solution of benzyl chloride (7.1 g, 0.056 mol) in 100 mL tetrahydrofuran. The reaction mixture was heated to reflux for 48 hours, then cooled to room temperature and concentrated in vacuo. The residue was taken up in 300 mL chloroform and washed with 3×100 mL water. The organic layer was then stirred with 100 mL 2N NaOH solution for 30 minutes. The layers were separated and the aqueous layer was extracted further with 2×100 mL chloroform. The chloroform layers were combined, dried over sodium sulfate, filtered, and concentrated under vacuum. The resulting oil was further purified by chromatography, eluting with hexane/ethyl acetate. 5.8 g of a clear oil was isolated which was characterized by analytical and spectroscopic properties as the hydrochloride salt, mp 250–253° C.

Analysis for $C_{21}H_{21}N \cdot HCl$: Calc'd: C=77.88, H=6.85, N=4.32, Cl=10.95. Found: C=77.97, H=6.90, N=4.14, Cl=10.94.

Step B: Preparation of
N'-(2,4-difluorophenyl)-N-benzyl-N-[(2,2-diphenyl)ethyl]urea.

To a solution of N-benzyl-2,2-diphenyl ethyl amine (1.5 g, 0.005 mol) in 100 mL ethyl acetate was added 2,4-difluorophenyl isocyanate (0.8 g, 0.005 mol). The mixture was stirred for 20 hours at room temperature and then concentrated under vacuum. The residue was taken up in hexane. The solid suspension was filtered and oven-dried, affording 2.2 g of a fine white powder, mp 120–123° C.

Analysis for $C_{28}H_{24}F_2N_2O$: Calc'd: C=76.00, H=5.47, N=6.33, F=8.59. Found: C=76.08, H=5.53, N=6.27, F=9.23.

EXAMPLE 2

Preparation of
N'-[(2,6-dimethyl)phenyl]-N-benzyl-N-[(2,2-diphenyl)ethyl]urea

The title compound is prepared similarly to Example 1, mp 205–208° C.

Analysis for $C_{30}H_{30}H_2O$: Calc'd: C=82.91, H=6.96, N=6.45. Found: C=82.79, H=7.00, N=6.19.

EXAMPLE 3

Preparation of
N'-[2,6-bis(1-methylethyl)phenyl]-N-benzyl-N-[(2,2-diphenyl)ethyl]urea The title compound is prepared similarly to Example 1, mp 153–155° C.

Analysis for $C_{34}H_{38}N_2O$: Calc'd: C=83.22, H=7.81, N=5.71. Found: C=83.32, H=7.78, N=5.56.

EXAMPLE 4

Preparation of
N'-(2,4-difluorophenyl)-N-benzyl-N-[(1-phenylcyclopentyl)methyl]urea The title compound is prepared similarly to Example 1, mp 119–122° C.

Analysis for $C_{26}H_{26}F_2N_2O$: Calc'd: C=74.27, H=6.23, N=6.66, F=9.04. Found: C=74.02, H=6.13, N=6.56, F=8.74.

EXAMPLE 5

Preparation of
N'-(2,6-dichlorophenyl)-N-benzyl-N-[(1-phenylcyclopentyl)methyl]urea The title compound is prepared similarly to Example 1, mp 125–127° C.

Analysis for $C_{26}H_{26}Cl_2N_2O$: Calc'd: C=68.88, H=5.78, N=6.18, Cl=15.64. Found: C=68.84, H=5.65, N=6.01, Cl=15.79.

EXAMPLE 6

Preparation of
N'-(2,4,6-trimethylphenyl)-N-benzyl-N-[(1-phenylcyclopentyl)methyl]urea The title compound is prepared in a similar manner as in Example 1, mp212-214° C.

Analysis for $C_{29}H_{34}N_2$: Calc'd: C=81.65, H=8.03, N=6.57. Found: C=81.72, H=8.09, N=6.60.

EXAMPLE 7

Preparation of
N'-[2,6-bis(1-methylethyl)phenyl]-N-benzyl-N-[(1-phenylcyclopentyl)methyl]urea The title compound is prepared in a similar manner as Example 1, mp124-127° C.

Analysis for $C_{32}H_{40}N_2O$: Calc'd: C=82.01, H=8.60, N=5.98. Found: C=82.02, H=8.64, N=5.80.

EXAMPLE 8

Preparation of
N'-[(2,6-dimethyl)phenyl]-N-benzyl-N-[(1-phenylcyclopentyl)methyl]urea The title compound is prepared in a similar manner as in Example 1, mp200-202° C.

Analysis for $C_{28}H_{33}N_2O$: Calc'd: C=81.51, H=7.82, N=6.79. Found: C=81.69, H=7.95, N=6.87.

EXAMPLE 9

Preparation of
N'-[2,6-bis(1-methylethyl)phenyl]-N-heptyl-N-[(1phenylcyclopentyl)methyl]urea

Step A: Preparation of
1-phenyl-1-cyclopentane-N-heptyl carboxamide

1-Phenyl-1-cyclopentane carboxylic acid (19.02 g, 0.1M) was dissolved in 100 mL of thionylchloride. The mixture was stirred overnight at room temperature then heated to reflux for one hour. The cooled reaction mixture was concentrated in vacuo. Diethyl ether was added to the residue and the resulting solution was concentrated in vacuo.

The above acid chloride was taken up in 100 mL of diethyl ether. The resulting solution was added dropwise with stirring to a solution of heptyl amine (11.52 g, 0.1M) and triethyl amine (10.1 g;0.1M) in 100 ml diethyl ether. The reaction mixture was stirred at room temperature for four hours. The precipitated triethyl amine hydrochloride was filtered and washed well with ether. The combined ether filtrates were concentrated in vacuo to give 28.4 g (98.9%), of a colorless oil that solidified on standing, mp 48-50° C.

Step B: Preparation of
1-phenylcyclopentyl-N-heptylmethyl amine

1-Phenyl-1-cyclopentane-N-heptyl carboxamide (27.9 g, 0.097M) was dissolved in 200 ml diethyl ether. This solution was added rapidly to a suspension of lithium aluminum hydride (7.4 g, 0.194M) in 200 mL diethyl ether. After the addition was complete, the reaction mixture was stirred at reflux for an additional two hours. The reaction mixture was cooled to room temperature and the excess lithium aluminum hydride was decomposed by the cautious addition of 7.7 mL H$_2$O, 5.82 ml 20% NaOH, and 27.2 mL H$_2$O. The resulting white solid was filtered and washed well with ether. The combined ether filtrates were concentrated in vacuo and the residue distilled to yield 14.9 g (56.3%) of the title compound.

Step C: Preparation of
N'-[2,6-bisil-methylethyl)-phenyl]-N-heptyl-N-[(1-phenylcyclopentyl)-methyl]urea 1-Phenylcyclopentyl-N-heptylmethylamine (5.46 g; 0.02M) was dissolved in 75 mL of ethyl acetate. To this solution was added, with stirring, a solution of 2,6-diisopropyl phenyl isocyanate (4.06 g; 0.02M) in 25 mL of ethyl acetate. The reaction mixture was stirred at room temperature overnight, concentrated to dryness, and the resulting white solid was chromatographed on silica using hexane:ethyl acetate (8:2) as the eluant to yield 5.2 g of the title compound, mp 95-97° C.

Analysis for $C_{32}H_{48}N_2O$: Calc'd: C=80.62, H=10.15, N=5.88. Found: C=80.29 H=10.15, N=5.63.

EXAMPLE 10

Preparation of
N'-[(2,6-dimethyl)phenyl]-N-heptyl-N-[(1-phenylcyclopentyl)methyl urea The title compound is prepared in a similar manner to Example 9; mp153-154° C.

Analysis for $C_{28}H_{40}N_2O$: Calc'd: C=79.95, H=9.59, N=6.66. Found: C=79.83, H=9.74, N=6.66.

EXAMPLE 11

Preparation of
N'-(2,4-difluorophenyl)-N-heptyl-N-[(1-phenylcyclopentyl)methyl]urea The title compound is prepared in a similar manner to Example 9, mp88-90° C.

Analysis for $C_{26}H_{34}F_2N_2O$ ⅓ H$_2$O: Calc'd: C=71.86, H=8.04, N=6.44, F=8.73. Found: C=71.91, H=7.92, N=6.25, F=8.73.

EXAMPLE 12

N'-[(2,6-dimethyl)phenyl]-N-heptyl-N-[(2,2-diphenyl)ethyl]urea

The title compound is prepared in a similar manner to Example 9; mp171-173° C.

Analysis for $C_{30}H_{38}N_2O$: Calc'd: C=81.40, H=8.65, N=6.33. Found: C=81.12, H=8.70, N=6.20.

EXAMPLE 13

N'-(2,4-difluorophenyl)-N-heptyl-N-[(2,2-diphenyl)ethyl]urea

The title compound is prepared in a similar manner to Example 9; mp 76-78° C.

Analysis for $C_{28}H_{32}F_2N_2O$ ½H$_2$O: Calc'd: C=73.17, H=7.23, N=6.09. Found: C=73.10, H=7.10, N=6.05.

I claim:

1. A compound of the formula

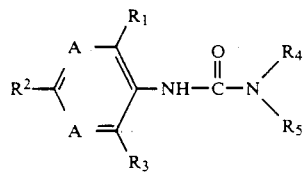

wherein
A is each independently CH or N;

$R_1$, $R_2$, and $R_3$ are each independently hydrogen, alkyl of one to six carbon atoms, halogen or alkoxy of one to six carbon atoms;

$R_4$ is alkyl of four to ten carbon atoms, cycloalkyl of three to seven carbon atoms, benzyl or benzyl substituted by alkyl of one to six carbon atoms, alkoxy of one to six carbon atoms, halogen, COOR' where R' is H, alkyl, $N_1'R_2'$ where $R_1'$ and $R_2'$ are each independently hydrogen, alkyl or cycloalkyl of three to seven carbon atoms, and $R_5$ is

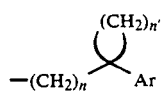

wherein n is 1;

n' is 4 or 5;

Ar is phenyl, naphthyl, pyridyl, thienyl or furanyl;

or a pharmaceutically acceptable acid addition or base salt thereof.

2. A compound as claimed in claim 1, wherein $R_4$ is alkyl of four to ten carbon atoms or benzyl.

3. A compound as claimed in claim 2, wherein $R_1$, $R_2$, and $R_3$ are each independently hydrogen, alkyl of one to six carbon atoms, fluorine or chlorine.

4. A compound as claimed in claim 3, wherein Ar is phenyl.

5. A compound as claimed in claim 4 and being N'-(2,4-difluorophenyl)-N-benzyl-N-[(1-phenylcyclopentyl)methyl]urea.

6. A compound as claimed in claim 4 and being N'-(2,6-dichlorophenyl)-N-benzyl-N-[(1-phenylcyclopentyl)methyl]urea.

7. A compound as claimed in claim 4 and being N'-(2,4,6-trimethylphenyl)-N-benzyl-N-[(1-phenylcyclopentyl)methyl]urea.

8. A compound as claimed in claim 4 and being N'-[(2,6-bis(1-methylethyl)phenyl]-N-benzyl-N-[(1-phenylcyclopentyl)methyl]urea.

9. A compound as claimed in claim 4 and being N'-[(2,6-dimethyl)phenyl]-N-benzyl-N-[(1-phenylcyclopentyl)methyl]urea.

10. A compound as claimed in claim 4 and being N'-[(2,6-bis(1-methylethyl)phenyl]-N-heptyl-N-[(1-phenylcyclopentyl)methyl]urea.

11. A compound as claimed in claim 4 and being N'-[(2,6-dimethyl)phenyl]-N-heptyl-N-[1-phenylcyclopentyl)methyl]urea.

12. A compound as claimed in claim 4 and being N'-(2,4-difluorophenyl)-N-heptyl-N-[(1-phenylcyclopentyl)methyl]urea.

13. A pharmaceutical composition for regulation cholesterol comprising an ACAT-inhibitory effective amount of a compound as claimed in claim 1 in combination with a pharmaceutically acceptable carrier.

14. A method of treating hypercholesterolemia and atherosclerosis comprising administering to a patient an ACAT-inhibitory effective amount of a compound as claimed in claim 1 in combination with a pharmaceutically acceptable carrier.

* * * * *